(12) United States Patent
Ahmed et al.

(10) Patent No.: US 8,852,634 B2
(45) Date of Patent: Oct. 7, 2014

(54) DOSAGE FORMULATION

(71) Applicant: Hoffmann-La Roche Inc., Nutley, NJ (US)

(72) Inventors: Hashim A. Ahmed, Wake Forest, NC (US); Susanne Page, Loerrach (DE); Navnit Hargovindas Shah, Clifton, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/787,870

(22) Filed: Mar. 7, 2013

(65) Prior Publication Data
US 2013/0189362 A1  Jul. 25, 2013

Related U.S. Application Data

(63) Continuation of application No. 12/954,970, filed on Nov. 29, 2010, now abandoned, which is a continuation of application No. 11/524,981, filed on Sep. 21, 2006, now abandoned.

(60) Provisional application No. 60/719,793, filed on Sep. 23, 2005.

(51) Int. Cl.
| | |
|---|---|
| *A61K 9/20* | (2006.01) |
| *A61K 9/28* | (2006.01) |
| *A61K 31/535* | (2006.01) |
| *B29B 9/06* | (2006.01) |
| *C07D 413/04* | (2006.01) |
| *A61K 31/445* | (2006.01) |
| *A61K 31/4427* | (2006.01) |
| *A61K 31/44* | (2006.01) |
| *A61K 31/455* | (2006.01) |
| *A61K 9/16* | (2006.01) |

(52) U.S. Cl.
CPC .............. *C07D 413/04* (2013.01); *A61K 9/1641* (2013.01); *A61K 31/445* (2013.01); *A61K 9/1694* (2013.01); *A61K 31/4427* (2013.01); *A61K 9/2095* (2013.01); *A61K 9/2031* (2013.01); *A61K 31/44* (2013.01); *A61K 31/455* (2013.01); *A61K 9/2077* (2013.01)
USPC ........ 424/464; 424/474; 514/235.5; 264/141; 427/2.14

(58) Field of Classification Search
CPC . A61K 9/2054; A61K 9/2866; A61K 9/2893; A61K 31/44; A61K 31/4427; A61K 31/445; A61K 9/1641; A61K 9/1694; A61K 9/2031; A61K 9/2077; A61K 9/2095; C07D 401/12; C07D 413/04; B29B 9/06
USPC ................ 424/464, 474; 514/235.5; 264/141; 427/2.14
See application file for complete search history.

(56) References Cited

U.S. PATENT DOCUMENTS

| | | |
|---|---|---|
| 4,764,361 A | 8/1988 | Bilski et al. |
| 5,281,420 A | 1/1994 | Kelm et al. |
| 5,387,595 A | 2/1995 | Mills et al. |
| 5,506,248 A | 4/1996 | Nikfar et al. |
| 5,554,633 A | 9/1996 | Teall |
| 5,612,337 A | 3/1997 | Baker et al. |
| 5,834,472 A | 11/1998 | Sangekar et al. |
| 5,972,938 A | 10/1999 | Rupniak et al. |
| 6,294,537 B1 | 9/2001 | Bichon et al. |
| 6,297,375 B1 | 10/2001 | Bos et al. |
| 6,303,790 B1 | 10/2001 | Hilpert et al. |
| 6,479,483 B2 | 11/2002 | Bos et al. |
| 6,706,281 B2 | 3/2004 | Oshlack et al. |

FOREIGN PATENT DOCUMENTS

| | | |
|---|---|---|
| CA | 2326529 | 5/2001 |
| EP | 089765 | 9/1983 |
| EP | 0235663 | 9/1987 |
| EP | 244080 | 11/1987 |
| EP | 244937 | 11/1987 |
| EP | 359547 | 3/1990 |
| EP | 0385350 | 9/1990 |
| EP | 0405931 | 1/1991 |
| EP | 427526 | 5/1991 |

(Continued)

OTHER PUBLICATIONS

Ikeura et al., Chem. Pharm. Bull. 45(10):1642-1652 ( 1997).
(Russian Office Action in corres. Russian Appl. No. 2008109823 Sep. 23, 2010).
(Abstract corresponding to WO 96/00213) 1996.
(Abstract correspond to WO 98/21185) 1998.
Longmore et al., "Canadian Journal of Physiology & Pharmacology" 75:612-621 (1997).
Schlecker et al., Tetrahedron 51(35):9531-9542 ( 1995).
World Pharmac: Synthetic Drug, Biochemical Drug and Formulation 18(3):192 ( 1997).

(Continued)

*Primary Examiner* — Aradhana Sasan

(57) ABSTRACT

The invention relates to a process for preparing a pharmaceutical tablet composition which comprises an active pharmaceutical ingredient of formula I

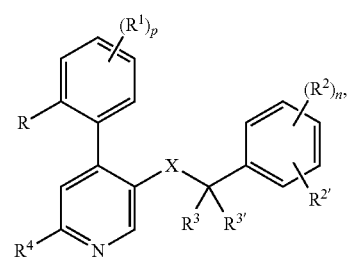

I wherein the definitions are described in claim 1, or pharmaceutically acceptable acid addition salts thereof and a water soluble poloxamer in which the compound of formula I and the water soluble poloxamer are processed by hot melt extrusion, and then the hot melt extrudate is mixed with other ingredients to form a tablet, that is optionally coated with a composition comprising an immediate release film coating system and purified water. The invention also relates to such pharmaceutical compositions and hot melt extrudates.

10 Claims, No Drawings

(56) References Cited

FOREIGN PATENT DOCUMENTS

| | | |
|---|---|---|
| EP | 524781 | 1/1993 |
| EP | 0638557 | 2/1995 |
| EP | 0733632 | 9/1996 |
| EP | 1035115 | 9/2000 |
| EP | 1103545 | 5/2001 |
| EP | 1103546 | 5/2001 |
| GB | 1557420 | 12/1979 |
| JP | 60-184008 | 9/1985 |
| JP | 10-512845 | 12/1998 |
| JP | 11-189546 | 7/1999 |
| JP | 200-247957 | 9/2000 |
| KR | 810320 | 10/1981 |
| KR | 8101697 | 10/1981 |
| WO | 92/06080 | 4/1992 |
| WO | 93/11110 | 6/1993 |
| WO | 94/21611 | 9/1994 |
| WO | 94/27604 | 12/1994 |
| WO | 95/16679 | 6/1995 |
| WO | 95/18124 | 7/1995 |
| WO | 95/23798 | 9/1995 |
| WO | 95/33744 | 12/1995 |
| WO | 96/00213 | 1/1996 |
| WO | 97/36871 | 10/1997 |
| WO | 98/21185 | 5/1998 |
| WO | 98/35681 | 8/1998 |
| WO | 00/50398 | 8/2000 |
| WO | 02/089835 | 11/2002 |

OTHER PUBLICATIONS (Translation of Japanese Office Action for JP 2008-531674 Sep. 27, 2011).
Maggi et al., "Autonomic & Autacoid Pharmacology" 13:23-93 (1993).
(abstract corresponding to WO 94/27604) 1994.
Navari et al., "The New England Journal of Medicine" 340(13):190-195 (1999).
Natsurgari et al., J. Med. Chem. 38(16):3106-3120 (1995).
Kramer et al., "Science" 281:1640-1645 (1998).
Barker, Reviews in the Nuerosciences 7(3):187-214 (1996).

DOSAGE FORMULATION

PRIORITY TO RELATED APPLICATIONS

This application is a continuation of U.S. application Ser. No. 12/954,970, filed Nov. 29, 2010, now abandoned, which is a continuation of U.S. application Ser. No. 11/524,981 filed Sep. 21, 2006, now abandoned; which claims the benefit of U.S. Provisional Application No. 60/719,793, filed Sep. 23, 2005. The entire contents of the above-identified applications are hereby incorporated by reference.

BACKGROUND OF THE INVENTION

Many substances obtained from modern drug discovery are problematic because of insufficient bioavailability. Such molecules often exhibit very low aqueous solubility and limited solubility in oils. Furthermore many substances exhibit significant food effects, i.e., when drugs and certain foods are taken at the same time they can interact in ways that diminish the effectiveness of the ingested drug or reduce the absorption of food nutrients. Additionally, vitamin and herbal supplements taken with prescribed medication can result in adverse reactions.

Some examples of how foods and drugs can interact include:

Food can speed up or slow down the action of a medication.

Impaired absorption of vitamins and minerals in the body.

Stimulation or suppression of the appetite.

Drugs may alter how nutrients are used in the body.

NK-1 receptor antagonists of formula I have been described in commonly owned EP 1,035,115 and U.S. Pat. No. 6,297,375

I wherein

R is lower alkyl, lower alkoxy, halogen or trifluoromethyl $R^1$ is halogen or hydrogen; and when p is 1, $R^1$ may in addition to the above substituents be taken together with R to form —CH=CH—CH=CH—;

$R^2$ and $R^{2'}$ are each independently hydrogen, halogen, trifluoromethyl, lower alkoxy or cyano;

and when n is 1, $R^2$ and $R^{2'}$ may in addition to the above substituents form —CH=CH—CH=CH—, unsubstituted or substituted by one or two substituents selected from lower alkyl or lower alkoxy;

$R^3$ and $R^{3'}$ are hydrogen, lower alkyl or taken together with the attached carbon atom form a cycloalkyl group;

$R^4$ is hydrogen, —N($R^5$)($CH_2$)$_n$OH, —N($R^5$)S(O)$_2$-lower alkyl, —N($R^5$)S(O)$_2$-phenyl, —N=CH—N($R^5$)$_2$, —N($R^5$)C(O)$R^5$, $R^5$ is hydrogen, $C_{3-6}$-cycloalkyl, benzyl, or lower alkyl;

$R^6$ is hydrogen, hydroxy, lower alkyl, —($CH_2$)$_n$COO—($R^5$), —N($R^5$)CO-lower alkyl, hydroxy-lower alkyl, —($CH_2$)$_n$CN, —($CH_2$)$_n$O($CH_2$)$_n$OH, —CHO or a 5- or 6-membered heterocyclic ring containing from 1 to 4 heteroatoms selected from the group consisting of oxygen, nitrogen, and sulfur, and with one of the carbon atoms in said ring being unsubstituted or substituted with an oxo group, which heterocyclic ring is directly bonded or bonded via an alkylene group to the remainder of the molecule;

is a cyclic tertiary amine which may contain one additional heteroatom selected from the group consisting of oxygen, nitrogen, or sulfur, wherein any sulfur present in the ring is thio or can be oxidized to sulfoxide or sulfur dioxide by which said cyclic tertiary amine is directly attached to the remainder of the molecule or is attached through the linker —($CH_2$)$_n$N($R^5$)—;

X is —C(O)N($R^5$)—, —($CH_2$)$_m$O—, —($CH_2$)$_m$N($R^S$)—, —N($R^5$)C(O)—, or —N($R^5$)($CH_2$)$_m$—;

n, p, and q are each independently 1 to 4; and m is 1 or 2;

and pharmaceutically acceptable acid addition salts thereof.

These compounds exist in crystalline form, which is practically insoluble in water (for example <0.0001 mg/ml) and in simulated gastric fluid (for example 0.08 mg/ml) at 25° C. They are active NK1 receptor antagonists, useful for the treatment of CNS disorders, such as depression, anxiety and emesis.

SUMMARY OF THE INVENTION

The bioavailability of a drug depends on several parameters, such as on the physicochemical nature of the active compound, the dosage form, and other physiological factors. Compounds of formula I are virtually insoluble in water and simulated gastric fluid, inhibiting oral bioavailability.

The present invention provides new galenic compositions for oral administration of pharmaceutically active compounds and a new process for preparing such galenic compositions. In particular, the compositions and process employ a hot melt extrusion of the active pharmaceutical ingredient and a poloxamer. The invention further provides hot melt extrudates of an active pharmaceutical ingredient and a poloxamer.

The oral dosage forms of the invention are suitable for delivery to human patients and are designed to enable sufficient availability of the active compound at its site of action. Such formulations may overcome the disadvantage of practical insolublility in simulated intestinal fluid for these compounds.

The process of the invention, provides, in particular, a process for preparing a pharmaceutical tablet composition, wherein the active pharmaceutical ingredient of formula I or pharmaceutically acceptable acid addition salts thereof and a water soluble poloxamer are processed by hot melt extrusion before mixing with the other ingredients. The tablet composition can thereafter be coated with a composition comprising an immediate release film coating system and purified water.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

The term "lower alkyl" denotes a straight- or branched-chain alkyl group containing from 1 to 7 carbon atoms. Nonlimiting examples of lower alkyl include methyl, ethyl, propyl, isopropyl, n-butyl, i-butyl, t-butyl, and the like.

The term "alkylene group" means a lower alkyl linker which is bound to a group at either end. Nonlimiting examples of alkylene groups include methylene, ethylene, propylene, and the like.

The term "lower alkoxy" denotes a alkyl group as defined above, which is attached through an oxygen atom. Nonlimiting examples of lower alkoxy groups include methoxy, ethoxy, propoxy, and the like.

The term "cycloalkyl" denotes a saturated carbocyclic group (e.g. a nonaromatic ring) containing 3 to 6 carbon atoms. Nonlimiting examples of cycloalkyl groups include cyclopropyl, cyclobutyl, cyclopentyl, cyclohexyl, and the like.

The term "halogen" denotes chlorine, iodine, fluorine, and bromine.

"Processing aids" are excipients that improve the manufacturability of the formulation by improving, for instance, flowability and by avoiding sticking.

One type of processing aid is colloidal silicon dioxide. "Colloidal silicon dioxide" is a submicroscopic fumed silica with a particle size of about 15 nm. It is a light, loose, bluish-white-colored, odorless, tasteless nongritty amorphous powder. Nonlimiting examples of colloid silicon dioxides useful in the invention include Aerosil 380 and Cab-O-Sil.

A "tablet filler/diluent" is a material that improves the bulk properties, e.g. mixing, flow, and compression, of a pharmaceutical formulation. They fill out the size of a tablet or capsule, making it practical to produce and convenient for consumer use. By increasing the bulk volume, the final product has the proper volume for patient handling. Nonlimiting examples of tablet filler/diluent include starch, modified starch derivatives, cellulose, calcium salts, sugar and sugar alcohols.

"Starch" is a substance consisting of amylase and amylopectin, two polysaccharides based on α-glucose. One type of starch that can be used in the invention is corn starch. Nonlimiting examples of corn starches that can be used in the invention include Pure-Cote, Pure-Bind, Pure-Dent, Pure-Gel, Pure-Set, Melojel, Meritena, Paygel55, Perfectamyl D6PH, Purity 21, Purity 826, and Tablet White.

One type of cellulose that can be used as tablet filler/diluent is microcrystalline cellulose. "Microcrystalline cellulose" (MCC) is a naturally occurring polymer comprised of a glucose units connected by a 1-4β glycosidic bond. MCC can be derived from a special grade of alpha cellulose. Nonlimiting examples of MCC that can be used in the invention include Avicel, Vivapur, Vivacel, Emcocel.

One type of sugar alcohol that can be used as tablet filler/diluent is mannitol. Nonlimiting examples of mannitol that can be used in the invention include Parteck M 200.

A "disintegrant" is a material that enhances the disintegrating properties of a pharmaceutical formulation. Typically, disintegrants expand, swell, and dissolve when wet, causing the tablet to break apart in the digestive tract, releasing the active ingredients for absorption. Different types of disintegrants such as NVP water-swellable polymers, croscarmellose, crospovidone and cellulose derivatives can be used in the invention. Nonlimiting examples of suitable disintegrants that can be used in the invention include Primellose and Polyplasdone.

A "glidant" is a material used to improve the flowability of the powder or granules or both.

An "NVP water-swellable polymer" is an insoluble, swellable homo- or heteropolymer containing N-vinylpyrrolidone, e.g. N-vinyl-2-pyrrolidone.

"Pharmaceutically acceptable acid addition salts" embraces salts with inorganic or organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Water-soluble poloxamers" are block copolymers of ethylene oxide, i.e. polyoxyethylene (POE), and propylene oxide, i.e. polyoxypropylene (POP), that are soluble in water and are used as wetting agents in pharmaceutical formulations. Nonlimiting examples of poloxamers useful in the present invention include Lutrol F68 (poloxamer 188).

"Extrusion" is the process of converting a raw material into a product of uniform shape and density by forcing it through a die under controlled conditions.

The present invention provides a composition which comprises a hot melt extrudate that comprises an active pharmaceutical ingredient and a water-soluble poloxamer. In particular, the invention provides a composition which comprises a hot melt extrudate that comprises a compound of formula I and a water soluble poloxamer, for example Lutrol F68.

A preferred compound of formula I is the compound, 2-(3, 5-bis-trifluoromethyl-phenyl)-N-methyl-N-(6-morpholin-4-yl-4-o-tolyl-pyridin-3-yl)-isobutyramide, having the structural formula

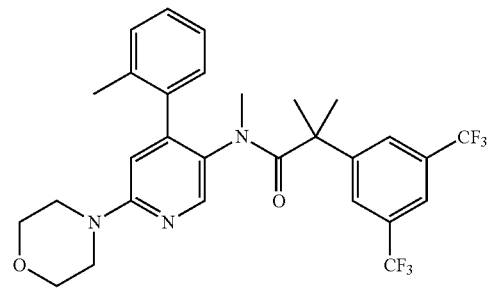 [SMILES: Cc1ccccc1-c1cc(N2CCOCC2)ncc1N(C)C(=O)C(C)(C)c1cc(C(F)(F)F)cc(C(F)(F)F)c1]

and which exhibits the above noted insolubilities, i.e. <0.0001 mg/ml in water and aqueous buffer solutions of pH 3.0-7.0.

In particular, the invention provides a composition comprising a hot melt extrudate that comprises a compound of formula I, such as 2-(3,5-bis-trifluoromethyl-phenyl)-N-methyl-N-(6-morpholin-4-yl-4-o-tolyl-pyridin-3-yl)-isobutyramidehydrochloride and a water-soluble poloxamer, such as Lutrol F68. A preferred form of the composition is a pharmaceutical tablet, such as a coated pharmaceutical tablet, in particular a 400 mg tablet.

The pharmaceutical tablet composition if the invention comprises

| | |
|---|---|
| a) an active ingredient of formula I | 30-60% |
| b) a water soluble poloxamer | 10-20% |
| c) a filler | 20-30% |
| d) a disintegrant | 1-10% |
| e) processing aid and | 0-5% and |
| f) glidant | 0-5%, and if desired |
| g) immediate release film coating system | 2-5% of the tablet weight |
| h) purified water | |

| An example of a representative formulation composition comprises the ingredients | mg/Tablet |
|---|---|
| 2-(3,5-Bis-trifluoromethyl-phenyl)-N-methyl-N-(6-morpholin-4-yl-4-o-tolyl-pyridin-3-yl)-isobutyramide hydrochloride | 400.00 |
| Lutrol F68 (Poloxamer 188) | 133.35 |
| Microcrystalline Cellulose (Avicel PH102) | 162.65 |
| Parteck M 200(Mannitol) | 30.00 |
| Polyplasdone XL (Crospovidone) | 16.00 |
| Colloidal Silicon Dioxide (Aerosil 380) | 16.00 |
| Corn Starch | 30.00 |
| Magnesium Stearate | 12.00 |
| Total Weight of Kernel | 800.00 |

| An example of a representative coating composition comprises | mg/Tablet |
|---|---|
| Opadry Yellow 03K 12429 | 25.00 |
| Purified Water | 131.25 |
| Total Weight of Film Coated Tablet | 825.00 |

The present invention also provides the hot melt extrudate employed in the composition. The extrudate comprises an active pharmaceutical ingredient and a poloxamer. In particular, the hot melt extrudate comprises a compound of formula I or a pharmaceutically acceptable salt thereof and a poloxamer. More particularly, the invention provides an extrudate of 2-(3,5-bis-trifluoromethyl-phenyl)-N-methyl-N-(6-morpholin-4-yl-4-o-tolyl-pyridin-3-yl)-isobutyramidehydrochloride and a water-soluble poloxamer, such as Lutrol F68.

The hot melt extrusion (HME) approach wherein the active pharmaceutical ingredient and a water soluble poloxamer, such as poloxamer 188 (Lutrol F68), a tablet binder and wetability agent are the only components which are processed through the extruder led to a microcrystalline solid dispersion having low particle size, acceptable particle dispersability, and dissolution characteristics that when the extrudate was combined with other excipients produced a tablet having the desired drug dissolution characteristics.

Manufacturing Process:

The invention provides a process for the manufacture of an extrudate that comprises an active pharmaceutical ingredient and a poloxamer which comprises
1) blending the active pharmaceutical ingredient with a water soluble poloxamer to form a powder blend,
2) extruding the powder blend from step 1) to form a hot melt extrudate, and
3) collecting the hot melt extrudate at room temperature.

Blending of the active pharmaceutical ingredient and the poloxamer can be accomplished in any conventional manner. For example, the two ingredients can be placed in a mixer or blender, for example, a PK Bin or Bohle mixer, and mixed. Alternatively, a portion of the active pharmaceutical ingredient, for example, about 50%, can be mixed with the poloxamer, followed by addition of the remainder of the active pharmaceutical ingredient. The material is preferably mixed for a period of about 30 minutes.

In one embodiment, the invention provides a process for preparing an extrudate comprising 2-(3,5-bis-trifluoromethyl-phenyl)-N-methyl-N-(6-morpholin-4-yl-4-o-tolyl-pyridin-3-yl)-isobutyramidehydrochloride and Lutrol F68 which comprises blending 2-(3,5-bis-trifluoromethyl-phenyl)-N-methyl-N-(6-morpholin-4-yl-4-o-tolyl-pyridin-3-yl)-isobutyramidehydrochloride with Lutrol F68 to form a powder blend, extruding the powder blend from step 1) to form a hot melt extrudate, and collecting the hot melt extrudate at room temperature.

In another embodiment, the invention provides a process for preparation of an extrudate which comprises
1) placing about 50% of the active pharmaceutical ingredient/drug substance in a blender, e.g. PK, Bin or Bohle mixer,
2) adding the water soluble poloxamer, followed by the remainder of the drug substance,
3) mixing the material from step 2) for about 30 minutes to form a powder blend,
4) transferring the powder blend from step 3) into a hot melt extruder (e.g. Leistritz) using a hopper-feeder (e.g. K-Tron Soder),
5) extruding the powder blend through the hot melt extruder, and
6) collecting the hot melt extrudate at room temperature.

Optionally, the powder blend contains additional ingredients, such as a tablet binder and/or wettability agent. Optionally, the hot melt extrudate can be passed through a sieving machine to obtain milled material, whereby more than one sieving step may be necessary to obtain material in the desired particle size range.

The present invention further provides a process for preparing a pharmaceutical tablet composition which comprises:
1) blending the active pharmaceutical ingredient with a water soluble poloxamer to form a powder blend,
2) extruding the powder blend from step 1) to form a hot melt extrudate,
3) passing the hot melt extrudate through a sieving machine to obtain milled material, whereby more than one sieving step may be necessary to obtain material in the desired particle size range,
4) blending the milled extrudate from step 3) with a filler(s) and a disintegrant,
5) blending the mixture from step 4) with a processing aid and a glidant, and
6) compressing the final blend prepared in step 5) into tablets.

In one embodiment, the invention provides a process for preparing a pharmaceutical tablet composition which comprises:
1) blending 2-(3,5-bis-trifluoromethyl-phenyl)-N-methyl-N-(6-morpholin-4-yl-4-o-tolyl-pyridin-3-yl)-isobutyramidehydrochloride with Lutrol F68 to form a powder blend,
2) extruding the powder blend from step 1) to form a hot melt extrudate,
3) passing the hot melt extrudate through a sieving machine to obtain milled material, whereby more than one sieving step may be necessary to obtain material in the desired particle size range,
4) blending the milled extrudate from step 3) with a filler(s) and a disintegrant,
5) blending the mixture from step 4) with a processing aid and a glidant, and 6) compressing the final blend prepared in step 5) into tablets.

In another embodiment, the process comprises:
1) placing about 50% of the active pharmaceutical ingredient/drug substance in a blender, e.g. PK, Bin or Bohle mixer,
2) adding the water soluble poloxamer, followed by the remainder of the drug substance,
3) mixing the material from step 2) for about 30 minutes to form a powder blend,
4) transferring the powder blend from step 3) into a hot melt extruder (e.g. Leistritz) using a hopper-feeder (e.g. K-Tron Soder)
5) extruding the powder blend through the hot melt extruder,
6) collecting the hot melt extrudate at room temperature,
7) passing the hot melt extrudate through a sieving machine, e.g. FitzMill, on a first pass set using slow speed knives forward through a #3 screen and then a second pass at medium speed knives forward through a #2 screen,
8) placing about 50% of the milled material in a PK blender or equivalent along with a filler (e.g. Avicel PH 102 or Parteck M 200, after passing through a #40 mesh screen), Corn Starch, a disintegrant (e.g. Polyplasdone XL), and other excipients (e.g. Aerosil, 380 after passing through a #12 mesh screen),
9) adding the remaining milled material and mixing for about 30 minutes to produce a powder mixture,
10) removing about 50% of the powder mixture,
11) adding a glidant (e.g. Magnesiun Stereate, after passing through a #40 mesh screen) to the remaining material in the blender, followed by readding the balance of the powder mixture and mixing for about 5 minutes, and
12) compressing the final blend into to tablets using, for instance, a 0.738"×0.344" oval shaped punches.

The kernels (tablets) can be coated as follows:
1) dispersing a complete film coating system, e.g. the Opadry Yellow, in purified water in a stainless steel container by mixing for 45 minutes until completely dispersed to form a coating suspension,
2) placing the kernels into a perforated coating pan and heating with inlet air of 45°+/−5° C. with intermittent jogging until the exhaust air reaches 40°+/−5° C.,
3) increasing the inlet temperature to 60°+/−5° C. and coating the kernels with the coating suspension, stirring continuously, and using an air spray system to apply a certain amount of the film coat (approx. 2 to 5% of the tablet weight) on a dry basis per tablet,
4) drying the coated tablets by jogging until the moisture content is less than 2%, and
5) cooling the tablets to room temperature and storing in a tight double polyethylene-lined container.

The invention claimed is:
1. A pharmaceutical composition in the form of a tablet comprising the following components
a) hot melt extrudate of 30-60% of a compound of formula I

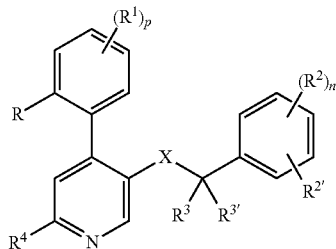

wherein
R is lower alkyl, lower alkoxy, halogen or trifluoromethyl
$R^1$ is halogen or hydrogen;

$R^2$ and $R^{2'}$ are each independently hydrogen, halogen, trifluoromethyl, lower alkoxy or cyano;
$R^4$ is

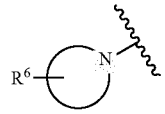

$R^5$ is hydrogen, $C_{3-6}$-cycloalkyl, benzyl, or lower alkyl;
$R^6$ is hydrogen, hydroxy, lower alkyl, —$(CH_2)_n$COO—$(R^5)$, —$N(R^5)$CO-lower alkyl, hydroxy-lower alkyl, —$(CH_2)_n$CN, —$(CH_2)_n$O$(CH_2)_n$OH, —CHO or a 5- or 6-membered heterocyclic ring containing from 1 to 4 heteroatoms selected from the group consisting of oxygen, nitrogen, and sulfur, and with one of the carbon atoms in said ring being
unsubstituted or substituted with an oxo group, which heterocyclic ring is directly bonded or bonded via an alkylene group to the remainder of the molecule;

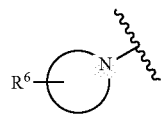

is a cyclic tertiary amine which may contain one additional heteroatom selected from the group consisting of oxygen, nitrogen, or sulfur, wherein any sulfur present in the ring is thio or can be oxidized to sulfoxide or sulfur dioxide by which said cyclic tertiary amine is directly attached to the remainder of the molecule;
X is —C(O)N($R^5$)— or —N($R^5$)C(O)—;
n and p are each independently 1 to 4;
or pharmaceutically acceptable acid addition salts thereof and 10-20% of a water soluble poloxamer;

| | |
|---|---|
| b) a filler | 20-30%; |
| c) a disintegrant | 1-10%; |
| d) processing aid | 0-5%; |
| e) glidant | 0-5%, and optionally |
| f) immediate release film coating system | 2-5% of the tablet weight; and |
| g) purified water, | | wherein the tablet contains 400 mg of the compound of Formula I.

2. A pharmaceutical composition of claim 1, wherein the compound of formula I is 2-(3,5-bis-trifluoromethyl-phenyl)-N-methyl-N-(6-morpholin-4-yl-4-o-tolyl-pyridin-3-yl)-isobutyramide.

3. A pharmaceutical composition of claim 1, wherein the water soluble poloxamer is poloxamer 188.

4. A pharmaceutical composition of claim 1, wherein the filler is a mixture of starch, microcrystalline cellulose and sugar alcohol.

5. A pharmaceutical composition of claim 4, wherein the filler is selected from the group consisting of corn starch, wheat starch, microcrystalline cellulose having a bulk density of 0.2-0.4 g/cc, microcrystalline cellulose having a bulk density of 0.4-0.6 g/cc, mannitol, and tablet white.

6. A pharmaceutical composition of claim 1, wherein the processing aid is colloidal silicon dioxide.

7. A pharmaceutical composition of claim 6, wherein the processing aid is a colloidal silicon dioxide having a surface area of 380 m²/g.

8. A pharmaceutical composition of claim 1, wherein the disintegrant is crospovidone.

9. A pharmaceutical composition of claim 1, wherein the glidant is magnesium stearate.

10. A pharmaceutical tablet composition according to claim 1, comprising

| | |
|---|---|
| 2-(3,5-Bis-trifluoromethyl-phenyl)-N-methyl-N-(6-morpholin-4-yl-4-o-tolyl-pyridin-3-yl)-isobutyramide hydrochloride | 400.00 mg |
| Poloxamer 188 | 133.35 mg |
| Microcrystalline Cellulose | 162.65 mg |
| Mannitol | 30.00 mg |
| Crosprovidone | 16.00 mg |
| Colloidal Silicon Dioxide | 16.00 mg |
| Corn Starch | 30.00 mg |
| Magnesium Stearate | 12.00 mg |
| film coating | 25.00 mg and |
| Purified Water | 131.25 ml. |

\* \* \* \* \*